US00PP07848P

United States Patent [19]

Stravers

[11] Patent Number: Plant 7,848

[45] Date of Patent: Mar. 31, 1992

[54] GERBERA PLANT NAMED TERFACCI

[75] Inventor: Lambertus J. M. Stravers, Kudelstaart, Netherlands

[73] Assignee: Terra Nigra BV, PA De Kwakel, Netherlands

[21] Appl. No.: 606,303

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner

[57] ABSTRACT

A new and distinct cultivar of Gerbera plant named Terfacci, characterized by its pastel orange ray floret color, green disc and both mature and immature flowers, inner band of yellow florets surrounding disc, and its single flower top and funnel-shaped flower form.

1 Drawing Sheet

1

The present invention comprises a new and distinct cultivar of Gerbera plant, botanically known as *Gerbera jamesonii,* and referred to by the cultivar name Terfacci.

Terfacci was originated from a hybridization made in a controlled breeding program in De Kwakel, The Netherlands in 1986 under the supervision of the inventor Lambertus J. M. Stravers.

The female parent was identified as "geell". The male parent was 83.151. The new cultivar was discovered and selected as one flowering plant within the progeny of the stated parentage by the inventor in or about January 1987 in a controlled environment in De Kwakel.

The first asexual reproduction of Terfacci was accomplished when vegetative cuttings were taken from the initial selection in April 1987 in a controlled environment in De Kwakel, The Netherlands by a technician working under formulations established and supervised by the inventor. The new cultivar is presently being propagated by cuttings and tissue culture. Horticultural examination of selected units initiated in November 1987 has demonstrated that the combination of characteristics as herein disclosed for Terfacci are firmly fixed and are retained through successive generations of asexual reproduction.

Terfacci has not been observed under all possible environmental conditions. The phenotype may vary significantly with variations in environment such as temperature, light intensity and day length. The following observations, measurements and comparisons describe plants grown in the greenhouse of Terra Nigra BV in De Kwakel, The Netherlands under controlled conditions which closely approximate those generally used in commercial practice.

The following traits have been repeatedly observed and have been determined to be basic characteristics of Terfacci, which in combination provide a new and distinct cultivar:

1. Pastel orange ray floret color.
2. Green disc, both immature and mature.
3. Yellow band of inner florets surrounding disc.
4. Single flower type, and generally funnel-shaped flower form.

Of the many commercial cultivars known to the present inventor, there is no cultivar sufficiently similar to Terfacci so as to provide a meaningful basis for comparison.

2

The accompanying photographic drawing shows typical inflorescence characteristics of Terfacci, with the colors being as nearly true as possible with illustrations of this type. The foliage of Terfacci is described in detail below but is not illustrated. The photograph comprises a closeup view of the novel flower form and color of the new cultivar.

In the following description, color references are made to The Royal Horticultural Society Colour Chart (R.H.S.). The color values were determined approximately mid day on Dec. 11, 1989 under artificial light at De Kwakel, The Netherlands.

Classification:

*Botanical.*—*Gerbera jamesonii* cv Terfacci.

*Commercial.*—Gerbera.

Parentage: Seedling from cross of cultivars designated "geell" and 83.151.

Plant: The plant when fully grown reaches a height of 40 cm.

Leaf blade:

*Length.*—Medium.

*Width.*—Medium.

*Thickenss.*—Medium.

*Blistering (puckering).*—Weak.

*Hairiness on upper side.*—Medium (midrib excluded.)

*Depth of cuts or incisions in leaf.*—Near bottom or base: Deep. Near middle: Medium. Near tip: Shallow.

*Color.*—Upper surface of leaf, medium green; lower surface, light green.

*Glossiness on upper side.*—Medium.

*Angle at tip.*—Weakly acute.

*Shape at tip.*—Pointed.

*Margin of lobes.*—Sinuate.

*Petiole length.*—Medium.

*Petiole anthocyanin coloration.*—Present, medium in intensity.

Peduncle:

*Length.*—Medium.

*Cross section.*—Round, medium strength and thickness.

*Resistance to bending.*—Medium.

*Hairiness.*—Dense.

*Color.*—Medium green.

*Anthocyanin.*—Present at base, strong in intensity; none present at tip.

*Bracts near tip.*—None.

Flower head:

*Type.*—Single; generally funnel shaped in form.

*Diameter from edge to edge.*—Medium; 10–11 cm. in diameter.

*Height.*—Distance from of attachment of involucre to top of flower head is medium.

*Involucre.*—Height: Medium. Diameter: Medium. Number of bracts: Medium; longitudinal aixs on inner rows are reflexing. Anthocyanin: Absent. Hairiness: Medium.

*Outer row ray florets.*—Number in outer row: Medium. Length of floret: Long. Width of floret: Broad. Shape of floret: Narrow, elliptic; longitudinal folding is medium. Shape of tip: Rounded, two teeth, medium in depth. Axis (longitudinal) of florets: Reflexing. Cross section of floret: Flat. Length of free petals: Long. Color distribution on inner side: Lighter towards base. Striation: Absent. Claw spot: Absent. Color on top side: 27C. Color on bottom side: 10D.

*Inner florets surrounding disc.*—Diameter: Relatively small. Color: Yellow. Longitudinal axis: Straight.

*Disc florets.*—Diameter: Medium. Main color of perianth lobes: Female flowers are red; male flowers are pink. Color (mature and immature): Green.

Reproductive parts:

*Stigma.*—Main color, white.

*Anthers.*—Main color, dark yellow; color at top lighter relative to other parts; longitudinal stripes are absent.

*Pappus.*—Main color: Yellow; uniform color throughout. Orientation: Level of top is above closed disc florets.

I claim:

1. A new and distinct cultivar of Gerbera plant named Terfacci, as illustrated and described.

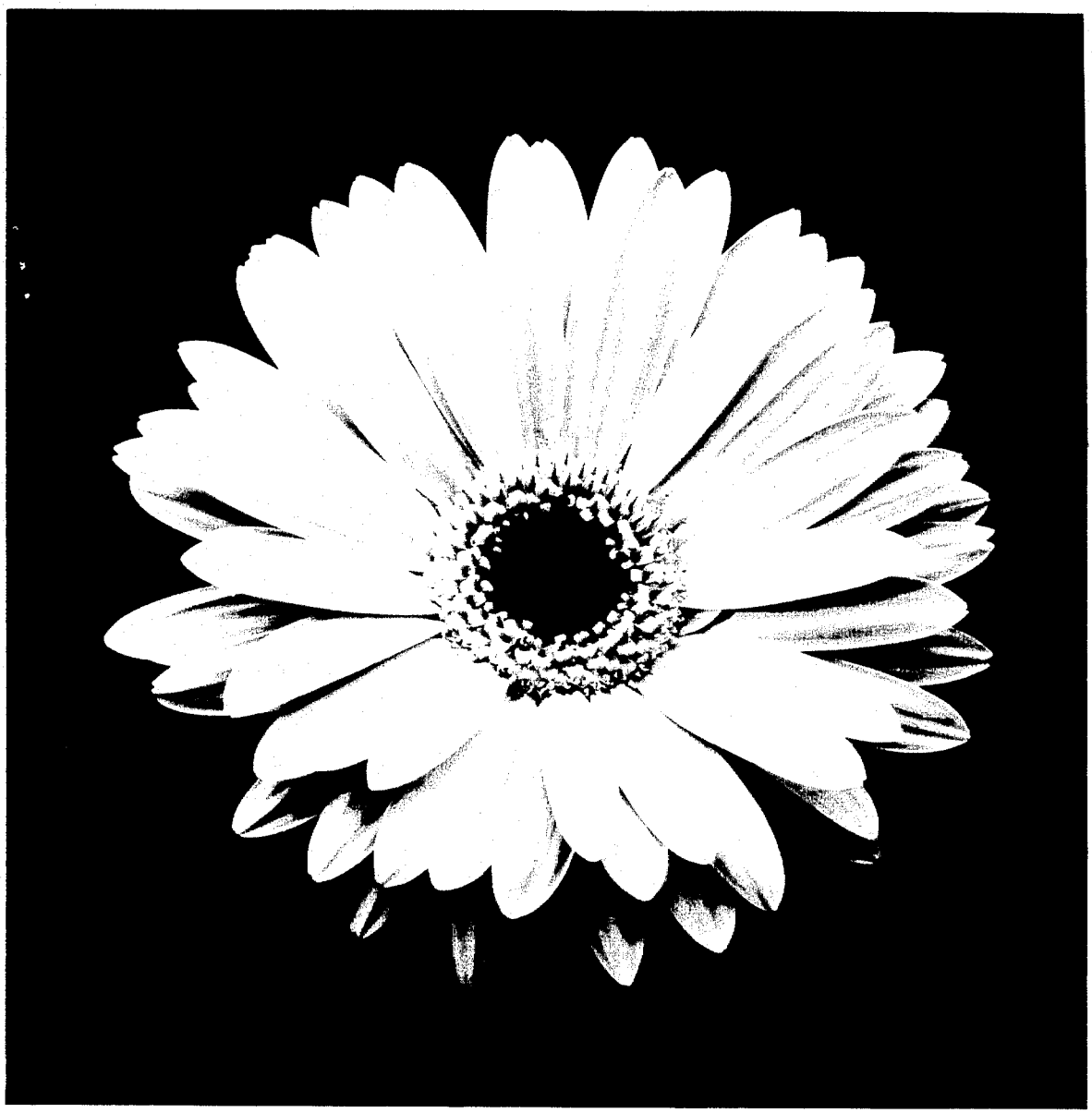

* * * * *